United States Patent [19]
Chevallet

[11] Patent Number: 5,200,627
[45] Date of Patent: Apr. 6, 1993

[54] APPARATUS AND METHOD FOR MONITORING FLOW OF INFUSION LIQUID

[75] Inventor: Jacques Chevallet, Serezin du Rhone, France

[73] Assignee: Hospal Industrie, France

[21] Appl. No.: 654,581

[22] Filed: Feb. 13, 1991

[30] Foreign Application Priority Data

Feb. 23, 1990 [FR] France .................................. 90 02548

[51] Int. Cl.⁵ .......................................... G01N 15/06
[52] U.S. Cl. .................................. 250/573; 250/576; 250/577
[58] Field of Search ............... 250/577, 576, 573, 565; 604/246; 356/436

[56] References Cited
U.S. PATENT DOCUMENTS 3,456,648 7/1969 Lee et al. .
3,907,437 9/1975 Hirschfeld ........................... 250/565

FOREIGN PATENT DOCUMENTS

WO89/12228 12/1989 World Int. Prop. O. .

OTHER PUBLICATIONS

IBM Technical Disclosure Bulletin, vol. 20, No. 4, Sep. 1977, pp. 1442-1443.

Primary Examiner—David C. Nelms
Assistant Examiner—T. Davenport
Attorney, Agent, or Firm—Finnegan, Henderson, Farabow, Garrett & Dunner

[57] ABSTRACT

The invention includes a blood detector disposed on a medical liquid duct adjacent a connection to a duct for circulating blood outside the body. When the medical liquid ceases to flow, blood sediments in the liquid duct and is detected therein. The detector makes it possible to verify that the medical liquid is indeed flowing into the blood. The invention is applicable in numerous blood treatment techniques making use of a circuit for circulating blood outside the body, such as hemofiltration, hemodiafiltration, and plasmapheresis.

13 Claims, 2 Drawing Sheets

APPARATUS AND METHOD FOR MONITORING FLOW OF INFUSION LIQUID

BACKGROUND OF THE INVENTION

1. Field of the Invention

The present invention relates to a detector for detecting the flow of a first liquid in a circuit for circulating a second liquid and, in particular, to a detector for detecting the flow of a medical liquid in a circuit for circulating blood outside the body.

2. Description of the Related Art

This invention is applicable in blood treatment techniques that make use of blood circulation outside the body and in which it is necessary to inject a medical liquid into the patient (for perfusion or for substitution purposes), which techniques include, for example, hemofiltration, hemodiafiltration, and plasmapheresis.

In these treatment techniques, the medical liquid is generally inserted into the blood in a circuit for circulating the blood outside the body, thereby avoiding the need to multiply direct accesses to the vascular system of the patient. Thus, in conventional medical liquid circuits, the duct along which the medical liquid flows from a supply of medical liquid is connected at one of its ends to one of the ducts in the blood circuit, either upstream or downstream of a blood treatment device.

An accident that occurs quite frequently in blood treatment installations of the type mentioned above, is an involuntary interruption in the flow of medical liquid, e.g. due to forgetting a clamp on a duct in the medical liquid circuit or due to stopping of the pump used for causing the medical liquid to flow and for adjusting its flow rate. An accident of this kind can have serious consequences for the patient if it is not detected quickly, and two main detection means are presently in use, either singly or in combination, for the purpose of detecting that the medical liquid is not flowing.

A first detection means used in medical liquid circuits including a flow pump is constituted by means for detecting pump rotation. Such detection means provide a partial solution only to the problem posed, since they serve to detect only one of the possible causes of the medical liquid flow being stopped, namely that the pump is stopped. In particular, such means cannot detect the presence of a clamp on a duct in the medical liquid circuit.

A second detection means that is used comprises a pressure detector responsive to the pressure in a degassing chamber which is generally provided in the medical liquid circuit, either upstream or downstream of the circulation pump, assuming the circuit includes one. Such detection means are also not reliable, since whether or not the detector can detect that there is no flow of medical liquid depends on the position of a clamp on the medical liquid duct relative to the degassing chamber and to the pump. For example, if a clamp is placed on that portion of the duct which extends between the degassing chamber and the pump, then there is no significant change in the pressure in the degassing chamber, regardless of whether the degassing chamber is disposed upstream or downstream from the pump relative to the flow direction of the medical liquid.

It should also be observed that the inadequacy of these detection means cannot be mitigated by using conventional flow detectors suitable for use on a medical liquid circuit. Given the special nature of a circuit of this type, namely that it is for use only once and that it is required to contain a sterile liquid which must not be polluted under any circumstances, a flow detector suitable for use on such a circuit must not have any part that comes into contact with the liquid, and more generally must be external to the medical liquid circuit. Unfortunately, conventional flow detectors of this type, e.g. ultrasonic detectors, are unsuitable for reliably detecting the flow of a liquid that is perfectly clear and that does not convey any particles or microbubbles.

SUMMARY OF THE INVENTION

An object of the present invention is to remedy these gaps in the state of the art and to provide means capable of reliably detecting the flow of a medical liquid in a circuit for circulating blood outside the body.

To achieve this object, the present invention provides a detector for detecting the flow of a first liquid designed to flow along first duct means into a second liquid designed to flow along second duct means to which the first duct means is connected, the detector comprising detector means for detecting the presence of the second liquid in the first duct means in the vicinity of its connection to the second duct means.

This detector is quite reliable in that it serves to monitor not only the existence of a flow along the medical liquid duct, but also that the medical liquid is effectively flowing into the blood.

In a first embodiment of the invention, the first and second duct means are constituted, in the vicinity of their interconnection, by tubes.

This flow detector has the advantage of being very easy to make and very inexpensive. It has also the advantage that merely by modifying its attitude, i.e. by modifying the slope relative to the horizontal of the terminal portion of the first duct, it is possible to adjust the threshold flow rate beneath which it triggers.

In a second embodiment of the invention, the second duct means includes a chamber and the first duct means is connected to the chamber at a level which is designed to be permanently occupied by the second liquid.

The invention also provides a detection device having an adjustable detection threshold, the device comprising a detector in accordance with the first embodiment specified above fixed to a turntable including means for holding the tubes relative to the detector means, the turntable being mounted to pivot relative to a support to enable the tube of the first duct means to be positioned in at least one position ranging from a horizontal position to a vertical position.

This detection device has the advantage of providing a detection threshold which is adjustable merely by pivoting the turntable (with the threshold corresponding to a determined rate of flow for the medical liquid through the interconnection between the ducts, with blood penetrating into the first duct when the flow rate drops below the threshold).

Other characteristics and advantages of the present invention appear from reading the following description. Reference is made to the accompanying drawings, in which:

FIGS. 1 to 3a and b are diagrammatic section views in a plane substantially containing the axes of both ducts and showing three different positions of a first embodiment of the invention;

FIG. 4 is a diagrammatic elevation view of a flow detector of the invention having an adjustable detection threshold; and FIG. 5 is a diagrammatic section view in a plane containing the axes of the ducts, showing a second embodiment of the invention.

DESCRIPTION OF THE PREFERRED EMBODIMENTS

Figure 2A:
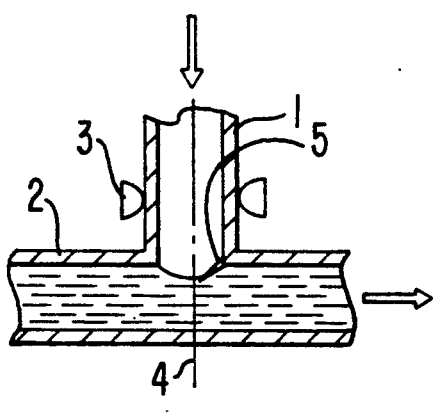
Figure 2B:
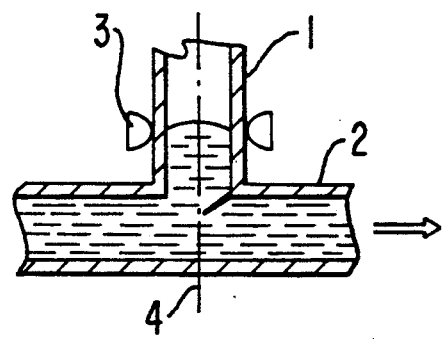
Figure 3A:
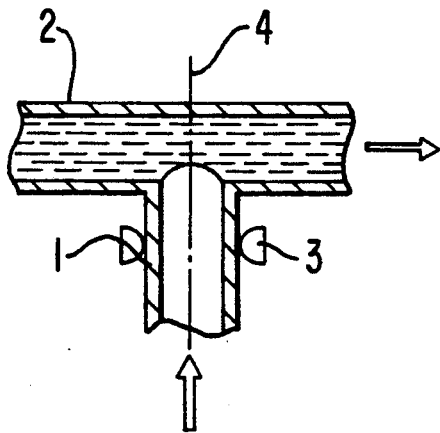
Figure 3B:
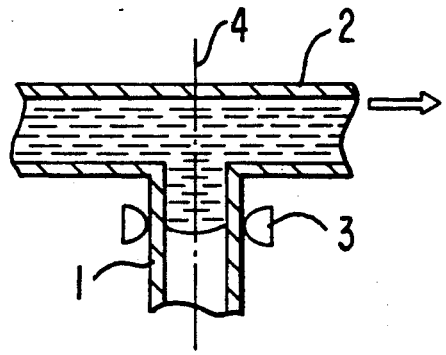

FIGS. 1 to 3 show the connection of the end portion of first duct means 1 (which may also be referred to as either an infusion line or as infusion duct means) for conveying a flow of a medical liquid to a tubular portion 2 of second duct means (which may also be referred to as receiving duct means) constituting a portion of a circuit for circulating blood outside the body. The terminal portion of the first duct means 1 is constituted by a flexible tube. In accordance with the invention, a first type of medical liquid flow detector is constituted by a blood detector 3 disposed on the tube 1 in the vicinity of the tube 2 substantially to intercept the axis 4 of the duct 1. The distance between the blood detector 3 and the tube 2 may be adjusted as a function of the response time desired for the flow detector. As explained in greater detail below, when describing the operation of the flow detector, if a minimum response time is desired, then the blood detector 3 is placed as close as possible to the tube 2, given the physical size of the selected blood detector.

The blood detector 3 may be constituted by any conventional detector capable of detecting the presence of a liquid in a duct, for example it may be an optical detector delivering colorimetry or turbidimetry data (in which case the tube 1 should be made of transparent material), or else it may be an inductive detector or a capacitive detector. Because optical detectors are reliable and inexpensive, it is particularly advantageous to use an optical detector in the detector of the invention.

The operation of this detector is based on taking advantage of two characteristics of blood: first its facility for sedimenting quickly when it is not in a position to coagulate; and second its facility of diffusing rapidly in an aqueous medium (naturally, blood is not the only liquid possessing one or both of these characteristics). Because of these characteristics of blood and as can be seen from FIGS. 1, 2, and 3, there is no need for the medical liquid tube 1 to have a special orientation in the space to ensure that a detector of the invention operates.

Figure 1A:
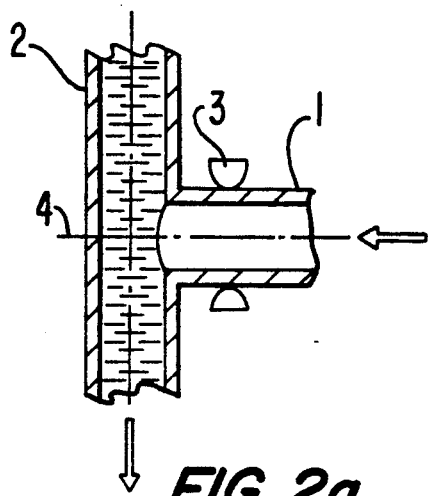
Figure 1B:
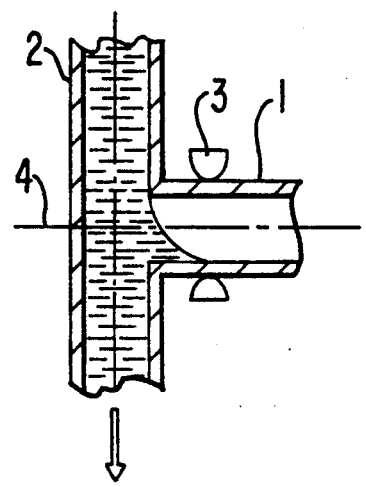

In FIG. 1, the axis 4 of the tube 1 is substantially horizontal. The tube 2 conveys a flow of blood, and so long as the medical liquid flows along the tube 1 and makes contact with the blood at a certain speed (FIG. 1a), then the medical liquid prevents the blood from penetrating into the tube 1. If the speed of the medical liquid falls below a certain value, then the blood in contact with the medical liquid stagnates in the tube 1 and almost immediately begins to sediment, penetrating into the tube 1 (FIG. 1b). When it reaches the detector 3 its presence is detected, thereby enabling an alarm to be triggered. For example, using tubes 1 and 2 having an inside diameter of about 4.5 mm, the medical liquid flow rate beneath which blood sediments is about 50 milliliters/hour (ml/h). With the ducts in the configuration shown, and with the detector 3 disposed about 5 mm from the end of the tube 1, blood takes about 5 seconds to reach the detector 3 from the moment the medical liquid ceases to flow.

In FIG. 2, the axis 4 of the medical liquid tube 1 is substantially vertical and the medical liquid comes in from above. The coupling between the ducts 1 and 2 advantageously includes a fin 5 extending over a portion of the downstream junction zone of the ducts (downstream relative to the blood flow direction), said fin projecting into the tube 2 a little way and at an angle, thereby tending to deflect a peripheral stream of the blood flowing along the tube 2 into the tube 1. So long as the velocity of the medical liquid at the junction between the ducts exceeds a threshold value, then the tendency of the fin 5 to deflect blood is overcome (FIG. 2a). However, if the velocity of the medical liquid falls below the threshold value, then the medical liquid no longer prevents blood being deflected by the fin 5, in which case blood spreads quickly by convection into the tube 1 where it is detected by the blood detector 3 (FIG. 2b).

In FIG. 3, the axis 4 of the medical liquid tube 1 is substantially vertical and the liquid arrives from below. The medical liquid flow detector operates in this position in the same manner as in the position shown in FIG. 1, except insofar as the medical liquid threshold velocity below which blood begins to sediment (other things being equal) is now much higher. For example, using a blood detector 3 placed on a tube 1 having an inside diameter of about 4.5 mm and at a distance of about 5 mm from a tube 2, likewise having an inside diameter of about 4.5 mm, as in the example given above with reference to FIG. 1, the threshold velocity is no longer about 50 ml/h but about 500 ml/h. Naturally, for unchanging medical liquid flow rate, the threshold value can be reduced by using a tube 1 of smaller diameter.

Figure 4:
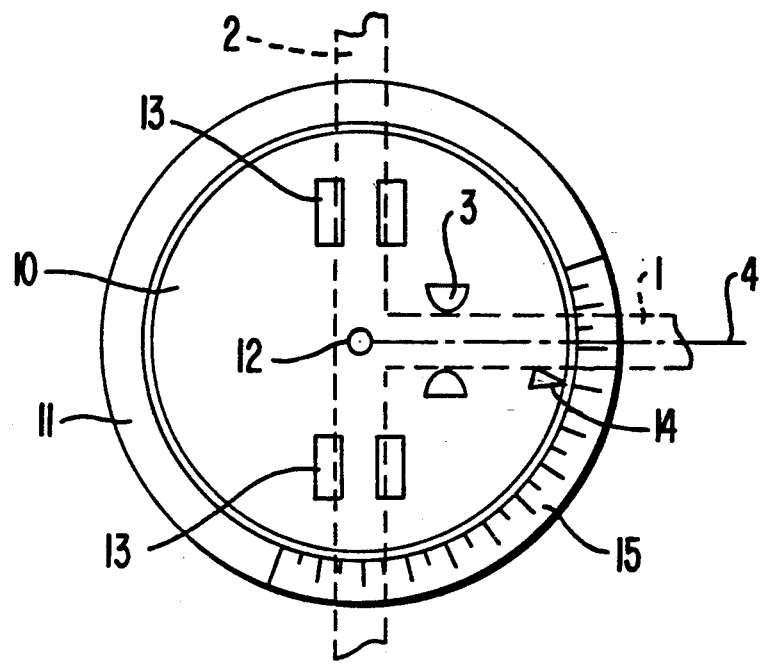

FIG. 4 shows a medical liquid flow rate detector device having an adjustable trigger threshold. This device includes a circular turntable 10 pivotally mounted on a support 11 about an axis 12 passing through its center. The support 11 is designed to be fixed so that the pivot axis 12 is substantially horizontal (the support could also for an integral portion of some other apparatus). A blood detector 3 is fixed on the turntable 10 to intercept a substantially radial direction. The turntable 10 includes two clamps 13 for retaining a tube 2 of a blood circuit to which the medical liquid circuit tube 1 is connected, in such a configuration that the tube 1 extends along the radial direction intercepted by the detector 3 and the detector 3 is close to the tube 2. Finally, the turntable 10 includes a mark 14 on its periphery disposed adjacent to a graduated sector 15 fixed relative to the support 11. In the embodiment shown, the graduated sector extends over one-fourth of a circle and corresponds to positions of a medical liquid circuit tube 1 ranging from horizontal to vertical, in which case the medical liquid comes in from below. Variations on this disposition include providing a graduated sector over one-fourth of a circle corresponding to positions of the tube 2 ranging from horizontal to vertical with the liquid coming in from above, or providing a graduated sector extending over a semicircle corresponding to all of the positions that the tube 2 can take up in a vertical plane.

Advantageously, the graduations on the sector 15 correspond to threshold flow rates below which the detection device triggers an alarm for a given type of duct (inside diameter) and for a given type of inter-duct connection (T-junction or Y-junction, optional presence of a fin 5).

Figure 5:
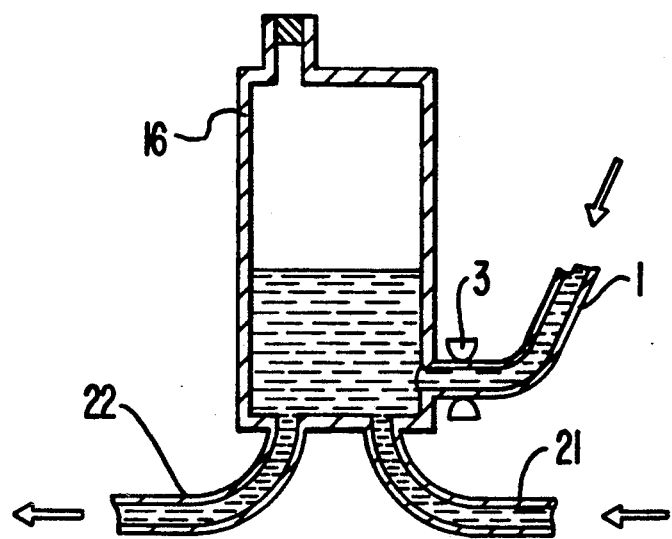

FIG. 5 shows a second embodiment of a medical liquid flow detector of the invention.

In this embodiment, the second duct means provided for blood circulation includes a chamber 16 which may be a degassing chamber. The base of the chamber has a first flexible tube 21 connected thereto, whereby blood penetrates into the chamber and a second flexible tube 22 connected thereto whereby blood leaves the chamber 16. The chamber also has the first duct means for the medical liquid flow connected thereto via an end which is constituted by a flexible tube 1. The flexible tube 1 is connected to the chamber 16 at a level where the chamber always contains blood in normal operation. A blood detector 3 is disposed on the tube 1 close to its connection to the chamber 16. The distance between the blood detector 3 and the chamber 16 may be adjusted as a function of the response time desired of the flow detector.

This second embodiment of the invention operates in the same manner as that described with reference to FIG. 1.

The invention is not limited to the embodiments described above and numerous variants may be made thereto by the person skilled in the art. In particular, the detector according to the invention can be use for others purposes than to detect the flow of a medical liquid into an extracorporal blood circuit. For example, it can be use to detect, in a perfusion set, the flow of a first medical liquid into a second medical liquid circulating in a duct connected to a patient, said liquids having to be mixed just before the infusion and one of the liquid being transparent and the other being coloured.

I claim:

1. A flow detecting apparatus for detecting movement of an infusion fluid into the flow of a receiving fluid, the apparatus comprising:
   receiving duct means for conveying the receiving fluid;
   infusion duct means connected to the receiving duct means for conveying the infusion fluid in an infusion direction into the receiving duct means; and
   means for sensing whether the receiving fluid moves from the receiving duct means into the infusion duct means in a direction opposite to the infusion direction.

2. An apparatus according to claim 1 wherein the receiving duct means and the infusion duct means respectively includes two tubes, the two tubes being connected to each other.

3. An apparatus according to claim 1 wherein the receiving duct means includes a chamber and the infusion duct means includes a tube, the tube being connected to the chamber.

4. An apparatus according to claim 1 wherein the sensing means includes an optical detector.

5. An apparatus according to claim 1 wherein the infusion duct means is connected to the receiving duct means at an infusion location, the apparatus further comprising means for selectively varying a spacial orientation of the infusion location in order to selectively alter flow characteristics of the receiving fluid relative to the infusion fluid.

6. A flow detecting apparatus for monitoring a flow of an infusion liquid into a flow of blood in an extracorporeal blood circuit, the apparatus comprising:
   blood duct means for conveying blood;
   infusion duct means connected to the blood duct means for conveying, in an infusion direction, an infusion liquid from a source into the blood duct means; and
   sensing means for sensing blood movement in said infusion duct means, in a direction opposite to said infusion direction.

7. An apparatus according to claim 6 wherein the infusion and blood duct means respectively include two tubes, the two tubes being connected to each other.

8. An apparatus according to claim 6 wherein the infusion duct means includes a tube and the blood duct means includes a degassing chamber, the tube being connected to the chamber.

9. An apparatus according to claim 6 wherein the sensing means includes an optical detector.

10. A flow detection apparatus for detecting a flow of a first liquid into a flow of a second liquid, the apparatus comprising;
    first tubing means for conveying the first liquid;
    second tubing means for conveying the second liquid, the first tubing means being connected to the second tubing means;
    sensing means for sensing the second liquid in the first tubing means; and
    pivotable support means for holding the first and second tubing means relative to the sensing means, the pivotable support means for selectively positioning the first tubing means in positions ranging from a horizontal position to a vertical position in order to vary a flow detection threshold.

11. A method for monitoring the infusion of liquid into an extracorporeal blood circuit, the method comprising the steps of:
    flowing blood through an extracorporeal blood circuit;
    supplying an infusion liquid to the blood circuit through an infusion line connected to the blood circuit at an infusion location; and
    sensing the presence of blood in the infusion line.

12. A method according to claim 11 wherein the step of sensing employs an optical detector.

13. A method according to claim 11 further including the step of varying a spacial orientation of the infusion location to thereby alter relative flow characteristics of the blood relative to the infusion liquid.

* * * * *